(12) United States Patent
McNair

(10) Patent No.: US 11,961,612 B1
(45) Date of Patent: *Apr. 16, 2024

(54) DETERMINING HEALTH SERVICE PERFORMANCE VIA A HEALTH EXCHANGE

(71) Applicant: CERNER INNOVATION, INC., Kansas City, KS (US)

(72) Inventor: Douglas S. McNair, Seattle, WA (US)

(73) Assignee: Cerner Innovation, Inc., Kansas City, MO (US)

( * ) Notice: Subject to any disclaimer, the term of this patent is extended or adjusted under 35 U.S.C. 154(b) by 304 days.

This patent is subject to a terminal disclaimer.

(21) Appl. No.: 17/392,457

(22) Filed: Aug. 3, 2021

Related U.S. Application Data

(63) Continuation of application No. 15/713,158, filed on Sep. 22, 2017, now Pat. No. 11,094,412.

(60) Provisional application No. 62/389,495, filed on Feb. 29, 2016.

(51) Int. Cl.
| | |
|---|---|
| *G16H 40/20* | (2018.01) |
| *G06Q 10/0639* | (2023.01) |
| *G06Q 10/067* | (2023.01) |
| *G07F 17/32* | (2006.01) |
| *G16H 10/60* | (2018.01) |
| *G16H 50/70* | (2018.01) |
| *G16H 80/00* | (2018.01) |

(Continued)

(52) U.S. Cl.
CPC ......... *G16H 40/20* (2018.01); *G06Q 10/0639* (2013.01); *G06Q 10/067* (2013.01); *G07F 17/3244* (2013.01); *G16H 10/60* (2018.01); *G16H 50/70* (2018.01); *G16H 80/00* (2018.01); *G06F 7/02* (2013.01); *G06Q 50/34* (2013.01)

(58) Field of Classification Search
CPC ........ G16H 40/20; G16H 10/60; G16H 50/70; G16H 80/00; G06Q 10/0639; G06Q 10/067; G06Q 50/34; G07F 17/3244; G06F 7/02
USPC ............................................... 705/2
See application file for complete search history.

(56) References Cited

U.S. PATENT DOCUMENTS

| | | | | |
|---|---|---|---|---|
| 5,924,073 A | * | 7/1999 | Tyuluman | G16H 10/60 |
| | | | | 600/300 |
| 8,583,450 B2 | * | 11/2013 | Baker | G16Z 99/00 |
| | | | | 705/2 |

(Continued)

*Primary Examiner* — Michael Tomaszewski
(74) *Attorney, Agent, or Firm* — Kilpatrick Townsend & Stockton LLP

(57) ABSTRACT

Systems, methods and computer-readable media are provided for applying performance data (e.g., Electronic Clinical Quality Measures (eCQM), Pay-for-Performance (P4P) measures, Meaningful Use (MU) measures) to a fantasy league health exchange. In aspects, a set of patient data for patients is determined. The set of patient data corresponds to a time interval of treatment of the patients by a population of clinicians. In addition, performance data is determined. The performance data corresponds to the population of clinicians and is based on the set of patient data and the time interval. Further, a provider ranking is determined using a classification model determined from the performance data and from explanatory attributes. The provider ranking can be used to forecast or project future performance results for selected individual or group providers. Further, the provider rankings can be used for draft picks, roster submission, or bets placed in a fantasy league exchange system.

20 Claims, 10 Drawing Sheets

(51) Int. Cl.
*G06F 7/02* (2006.01)
*G06Q 50/34* (2012.01)

(56) References Cited

U.S. PATENT DOCUMENTS

| | | | |
|---|---|---|---|
| 8,666,774 B1 * | 3/2014 | Gonzales, Jr. | G16H 40/20 |
| | | | 705/2 |
| 11,094,412 B1 | 8/2021 | Mcnair | |
| 2006/0100904 A1 | 5/2006 | Jee et al. | |
| 2006/0161456 A1 * | 7/2006 | Baker | G16Z 99/00 |
| | | | 705/2 |
| 2008/0262882 A1 * | 10/2008 | Farrell | G06Q 10/06398 |
| | | | 705/7.41 |
| 2009/0125348 A1 * | 5/2009 | Rastogi | G06Q 30/0202 |
| | | | 705/7.32 |
| 2009/0259488 A1 * | 10/2009 | Gounares | G16H 70/20 |
| | | | 705/7.42 |
| 2010/0274580 A1 * | 10/2010 | Crownover | G06Q 10/06393 |
| | | | 705/2 |
| 2013/0275143 A1 | 10/2013 | Cadger et al. | |
| 2014/0244276 A1 | 8/2014 | Dyke et al. | |
| 2015/0006261 A1 * | 1/2015 | Gutman | G06F 3/0482 |
| | | | 705/7.39 |
| 2015/0019247 A1 | 1/2015 | Stedillie | |
| 2015/0073824 A1 * | 3/2015 | Norris | G16H 10/60 |
| | | | 705/2 |
| 2016/0063193 A1 | 3/2016 | Freese et al. | |
| 2016/0321593 A1 | 11/2016 | Gonos et al. | |
| 2017/0004548 A1 | 1/2017 | Goel et al. | |

* cited by examiner

```
################################################################

#  Parallelized Bradley-Terry modeling of eCQM performance for Fantasy Health wagering

########################################################## library(Matrix)
library(lme4)
library(BradleyTerry2)
library(gnm)
library(qvcalc)

# load dataset 2
predictors <- read.csv(file="c:/0_cerdsm/IP/eCQM_DFS/EP_predictors2.csv", header=TRUE,
            colClasses=c("integer",rep("numeric",16),"factor"))
predictors$id <- factor(predictors$id, labels=unique(predictors$id))

contests <- read.csv(file="c:/0_cerdsm/IP/eCQM_DFS/EP_contests2.csv", header=TRUE,
            colClasses=rep("integer",2))
contests$winner <- factor(contests$winner, levels=unique(predictors$id))
contests$loser <- factor(contests$loser, levels=unique(predictors$id))

# create result vector for projections
result <- rep(1, nrow(contests))

# explore effect sizes of predictors
BTmodel9 <- BTm(result, winner, loser, ~ CQM01[..] + CQM02[..] + CQM03[..] + CQM04[..] +
CQM05[..] + CQM06[..] + CQM07[..] + CQM08[..] + CQM09[..]
         + CQM10[..] + CQM11[..] + CQM12[..] + CQM13[..] + CQM14[..] + ALTPAY[..] + 5STAR[..] +
(1|..), data=list(contests, predictors), tol=1e-4, sigma=2, trace=FALSE)
summary(BTmodel9)

# determine Bradley-Terry model using strongest predictors
BTmodel1 <- BTm(result, winner, loser, ~ CQM01[..] + CQM03[..] + (1|..), data=list(contests,
predictors), tol=1e-4, sigma=2, trace=FALSE)
summary(BTmodel1)
# Fixed Effects:
Estimate Std. Error z value Pr(>|z|)
# ..96    3.127e+01 1.295e+06  0.000  1.0000
# ..99    1.814e+00 1.428e+00  1.271  0.2038
# CQM01[..] -1.938e+00 1.043e+00 -1.858  0.0632 .
# CQM03[..]  3.502e+00 1.559e+00  2.246  0.0247 *

# Random Effects:
Estimate Std. Error z value Pr(>|z|)
Std. Dev.  1.0720   0.2912  3.681 0.000232 *** drop one
drop1(BTmodel1, test="Chisq")
#         Statistic Df P(>|Chi|)
# `CQM01[..]`  3.4505 1  0.06323 .
`CQM03[..]`  5.0439 1  0.02471 * add one
add1(BTmodel1, ~ . + CQM12[..] + CQM13[..], test="Chisq")
#         Statistic Df P(>|Chi|)
# CQM12[..]  2.6063 1  0.10644
# CQM13[..]  4.5828 1  0.03229 *
```

CONTINUES IN FIG. 4B

*FIG. 4A*

CONTINUES FROM FIG. 4A

.
.

```
# re-calculate Bradley-Terry model
BTmodel2 <- update(BTmodel1, formula = ~ . + CQM13[..])
summary(BTmodel2)
# Fixed Effects:
Estimate Std. Error z value Pr(>|z|)
# ..96      2.870e+01  7.985e+05  0.000  0.99997
# ..99      5.108e-02  1.670e+00  0.031  0.97560
# CQM01[..] -2.217e+00 1.094e+00 -2.025  0.04283 *
# CQM03[..]  4.797e+00 1.775e+00  2.702  0.00688 **
# CQM13[..] -3.595e+00 1.680e+00 -2.141  0.03229 *

# Random Effects:
Estimate Std. Error z value Pr(>|z|)
Std. Dev.  1.102     0.312     3.532  0.000412 *** drop1(BTmodel2, test="Chisq")
Statistic Df P(>|Chi|)
# `CQM01[..]`  4.1020  1  0.042833 *
# `CQM03[..]`  7.3030  1  0.006884 **
`CQM13[..]`  4.5828  1  0.032294 * determine abilities of EPs
alpha <- BTabilities(BTmodel2)

plot(row.names(alpha), alpha$ability)

rnk <- sort(alpha[,1], decreasing=TRUE)
as.integer(attr(rnk, "names"))

################################### load dataset 3
predictors <- read.csv(file="c:/0_cerdsm/IP/eCQM_DFS/EP_predictors3.csv", header=TRUE,
          colClasses=c("integer",rep("numeric",16),"factor"))
predictors$id <- factor(predictors$id, labels=unique(predictors$id))

contests <- read.csv(file="c:/0_cerdsm/IP/eCQM_DFS/EP_contests3.csv", header=TRUE,
          colClasses=rep("integer",2))
contests$winner <- factor(contests$winner, levels=unique(predictors$id))
contests$loser <- factor(contests$loser, levels=unique(predictors$id))

# create result vector for projections
result <- rep(1, nrow(contests))

# explore effect sizes of predictors
BTmodel9 <- BTm(result, winner, loser, ~ CQM01[..] + CQM02[..] + CQM03[..] + CQM04[..] +
CQM05[..] + CQM06[..] + CQM07[..] + CQM08[..] + CQM09[..]
        + CQM10[..] + CQM11[..] + CQM12[..] + CQM13[..] + CQM14[..] + ALTPAY[..] +
5STAR[..] + (1|..), data=list(contests, predictors), tol=1e-4, sigma=2, trace=FALSE)
summary(BTmodel9)

# determine Bradley-Terry model using strongest predictors
BTmodel1 <- BTm(result, winner, loser, ~ CQM01[..] + CQM03[..] + (1|..), data=list(contests,
predictors), tol=1e-4, sigma=2, trace=FALSE)
summary(BTmodel1)
```

CONTINUES IN FIG. 4C

CONTINUES FROM FIG. 4B

.
.

```
# drop one
drop1(BTmodel1, test="Chisq")

# add one
add1(BTmodel1, ~ . + CQM12[..] + CQM13[..], test="Chisq")

# re-calculate Bradley-Terry model
BTmodel2 <- update(BTmodel1, formula = ~ . + CQM13[..])
summary(BTmodel2)

drop1(BTmodel2, test="Chisq")

# determine abilities of EPs
alpha <- BTabilities(BTmodel2)

plot(row.names(alpha), alpha$ability)

rnk <- sort(alpha[,1], decreasing=TRUE)
as.integer(attr(rnk, "names"))

################################### load dataset 4
predictors <- read.csv(file="c:/0_cerdsm/IP/eCQM_DFS/EP_predictors4.csv", header=TRUE,
            colClasses=c("integer",rep("numeric",16),"factor"))
predictors$id <- factor(predictors$id, labels=unique(predictors$id))

contests <- read.csv(file="c:/0_cerdsm/IP/eCQM_DFS/EP_contests4.csv", header=TRUE,
            colClasses=rep("integer",2))
contests$winner <- factor(contests$winner, levels=unique(predictors$id))
contests$loser <- factor(contests$loser, levels=unique(predictors$id))

# create result vector for projections
result <- rep(1, nrow(contests))

# explore effect sizes of predictors
BTmodel9 <- BTm(result, winner, loser, ~ CQM01[..] + CQM02[..] + CQM03[..] + CQM04[..] +
CQM05[..] + CQM06[..] + CQM07[..] + CQM08[..] + CQM09[..]
        + CQM10[..] + CQM11[..] + CQM12[..] + CQM13[..] + CQM14[..] + ALTPAY[..] +
5STAR[..] + (1|..), data=list(contests, predictors), tol=1e-4, sigma=2, trace=FALSE)
summary(BTmodel9)

# determine Bradley-Terry model using strongest predictors
BTmodel1 <- BTm(result, winner, loser, ~ CQM01[..] + CQM03[..] + (1|..), data=list(contests,
predictors), tol=1e-4, sigma=2, trace=FALSE)
summary(BTmodel1)
```

CONTINUES IN FIG. 4D

CONTINUES FROM FIG. 4C

.
.

```
# drop one
drop1(BTmodel1, test="Chisq")

# add one
add1(BTmodel1, ~ . + CQM12[..] + CQM13[..], test="Chisq")

# re-calculate Bradley-Terry model
BTmodel2 <- update(BTmodel1, formula = ~ . + CQM13[..])
summary(BTmodel2)

drop1(BTmodel2, test="Chisq")

# determine abilities of EPs
alpha <- BTabilities(BTmodel2)

plot(row.names(alpha), alpha$ability)

rnk <- sort(alpha[,1], decreasing=TRUE)
as.integer(attr(rnk, "names"))
```

*FIG. 4D*

```

Medicare.gov Physician Compare database National download flat files library(data.table)

load data 2014 - 2,034,813 rows (separate row for each claims-based affiliation) - 0.7GB - 70 sec to load
# 43 columns
# 1     2       3               4       5       6       7       8       9       10              11

# NPI, PAC ID, Professional Enrollment ID, Last Name, First Name, Middle Name, Suffix, Gender,
# Credential, Medical school name, Graduation year,
#   12              13              14              15              16              17

# Primary specialty, Secondary specialty 1, Secondary specialty 2, Secondary specialty 3, Secondary
# specialty 4, All secondary specialties,
#     18              19              20              21              22              23              24

# Organization legal name, Organization DBA name, Group Practice PAC ID, Number of Group Practice
# members, Line 1 Street Address, Line 2 Street Address, Marker addr line 2 suppression,
# 25   26   27              28              29                              30              31

# City, State, Zip Code, Claims based hospital affiliation CCN 1, Claims based hospital affiliation LBN 1,
# Claims based hospital affiliation CCN 2, Claims based hospital affiliation LBN 2,
#          32              33              34              35

# Claims based hospital affiliation CCN 3, Claims based hospital affiliation LBN 3, Claims based hospital
# affiliation CCN 4, Claims based hospital affiliation LBN 4,
#          36              37              38

# Claims based hospital affiliation CCN 5, Claims based hospital affiliation LBN 5, Professional accepts
# Medicare Assignment,
#      39        40              41              42                              43

# Participating in eRx, Participating in PQRS, Participating in EHR, Received PQRS Maintenance of
# Certification (MOC) Program Incentive, Participated in Million Hearts

# fast read fails on EOF exceptions, so use old read.table()
# pc2014 <- fread("c:/0_cerdsm/IP/eCQM_DFS/physician_compare/2014/National_2014.csv",
# header=FALSE, skip=1, sep=",",
colClasses=rep("character",43), data.table=FALSE)

pc2014 <- read.csv(file="c:/0_cerdsm/IP/eCQM_DFS/physician_compare/2014/National_2014.csv",
header=FALSE, skip=1, blank.lines.skip=TRUE, flush=TRUE,
               colClasses=rep("character",43))
pc2014.len <- length(pc2014[,1])

# load data 2015 - 2,193,582 rows (separate row for each claims-based affiliation) - 0.7GB - 15 sec to load
# fast read succeeds
pc2015 <- fread("c:/0_cerdsm/IP/eCQM_DFS/physician_compare/2015/National_2015.csv",
header=FALSE, skip=1, sep=",",
               colClasses=rep("character",43), data.table=FALSE)

# pc2015 <- read.csv(file="c:/0_cerdsm/IP/eCQM_DFS/physician_compare/2015/National_2015.csv",
header=FALSE, skip=1, blank.lines.skip=TRUE, flush=TRUE,
colClasses=rep("character",43))
pc2015.len <- length(pc2015[,1])
```

CONTINUES IN FIG. 5B

*FIG. 5A*

CONTINUES FROM FIG. 5A

```
# number of unique NPIs
length(unique(pc2014[,1]))   # 890,707
length(unique(pc2015[,1]))   # 905,136 number of unique primary specialties
length(unique(pc2014[,12]))  # 76
length(unique(pc2015[,12]))  # 77 calculate descriptive statistics
pc2014$erx      <- 0
pc2014$pqrs     <- 0
pc2014$ehr      <- 0 each sapply takes ~ 60 sec on 2 million rows
Sys.time()
pc2014$erx   <- sapply(pc2014[,39], function(x) as.integer(eval(x == "Y")))
pc2014$pqrs  <- sapply(pc2014[,40], function(x) as.integer(eval(x == "Y")))
pc2014$ehr   <- sapply(pc2014[,41], function(x) as.integer(eval(x == "Y")))

Sys.time()
pc2015$erx      <- 0
pc2015$pqrs     <- 0
pc2015$ehr      <- 0 pc2015$erx   <- sapply(pc2015[,39], function(x) as.integer(eval(x == "Y")))
pc2015$pqrs  <- sapply(pc2015[,40], function(x) as.integer(eval(x == "Y")))
pc2015$ehr   <- sapply(pc2015[,41], function(x) as.integer(eval(x == "Y")))

Sys.time()

paste0("eRx  - mean 2014   ", mean(pc2014$erx))    # 0.28
paste0(" ")

paste0("eRx  - mean 2015   ", mean(pc2015$erx))    # 0.26  14,429 more new EPs registered
in 2015 for PQRS/payment reasons but many not yet eRx-cert
paste0(" ")

paste0("PQRS - mean 2014   ", mean(pc2014$pqrs))   # 0.42
paste0(" ")

paste0("PQRS - mean 2015   ", mean(pc2015$pqrs))   # 0.44
paste0(" ")

paste0("EHR  - mean 2014   ", mean(pc2014$ehr))    # 0.29
paste0(" ")

paste0("EHR  - mean 2015   ", mean(pc2015$ehr))    # 0.28  14,429 more new EPs registered
in 2015 for PQRS/payment reasons but many not yet MU EHR-cert
paste0(" ")

# calculate correlation between PQRS and EHR incentives participation
paste0("PQRS-EHR corr 2014: ", cor(pc2014$pqrs,pc2014$ehr))  # 0.18
paste0("PQRS-EHR corr 2015: ", cor(pc2015$pqrs,pc2015$ehr))  # 0.31

DETERMINING HEALTH SERVICE PERFORMANCE VIA A HEALTH EXCHANGE

CROSS-REFERENCE TO RELATED APPLICATIONS

This application is a continuation of and claims priority to U.S. application Ser. No. 15/713,158, entitled "Determining Health Service Performance via a Heath Exchange," filed Sep. 22, 2017; which claims priority to U.S. Provisional Application No. 62/398,495, entitled "Health Services via Health Exchange," filed Sep. 22, 2016. The aforementioned applications are hereby incorporated by reference herein in their entirety.

BACKGROUND

With respect to health services finance, accurate and reliable quality measurement is increasingly important to public-sector federal and state payment strategies and to private-sector commercial payment strategies as well. A new generation of technical infrastructure is enabling payers in both sectors to define and identify high-value service delivery. Recent reforms, including the Affordable Care Act of 2010, are pushing payers to become more prudent purchasers of care, spurring them to implement payment strategies that reward value in the health care system.

The U.S. federal Medicare program, despite its historical reputation of being a payer with little regard to the value of the services it buys, has recently put in place a range of programs aimed at assessing quality and value, coupled with financial incentives for those whose assessments indicate superior performance and financial penalties for those whose performance is inferior or falls below normative target levels. Such programs are called 'Pay for Performance' (P4P) or 'Pay for Value' (P4V) programs. More such programs are expected to be forthcoming. The issues surrounding these programs are complex, and it is no surprise that there is a level of contention between providers and regulators and payors, even though all parties profess committedness to improved health services quality. Participation in all Clinical Quality Measures (CQM) programs is, to date, voluntary. However, a decision not to participate increasingly carries a financial penalty, as payors try to encourage behavior they cannot force.

Various jurisdictions are becoming increasingly sensitive to their annual spending on health services, to the opportunities to offset those expenditures with improvements in quality and safety and other aspects of value, and to the need for health information technology (health IT) in order to fully leverage those opportunities. And, like other health care providers exploring health IT implementation, they are weighing whether to participate in the incentive programs to promote adoption of electronic health record (EHR) systems, which are commonly referred to as "meaningful use" ('MU'). MU is the linchpin of the Medicare and Medicaid EHR Incentive Programs, established under the U.S. Health Information Technology for Economic and Clinical Health (HITECH) Act, enacted as part of the American Recovery and Reinvestment Act of 2009. Providers demonstrate meaningful use by "attesting" to certain criteria for different stages of MU, and the attestations may be audited to determine the veracity of the attestations.

The U.S. Tax Relief and Health Care Act of 2006 required the establishment of a quality reporting system for eligible health care professionals, incorporating an incentive payment for those who satisfactorily report data on quality measures for covered professional services furnished to Medicare beneficiaries. Though the Centers for Medicare & Medicaid Services (CMS) named it the Physician Quality Reporting Initiative (PQRI), eligible professionals also include physician assistants, advanced practice registered nurses, licensed social workers, clinical psychologists, and others such as speech and physical therapists. Under the Patient Protection and Affordable Care Act of 2010 (ACA), there was a name change to the Physician Quality Reporting System (PQRS).

By 2015, there were 300 individual measures established in the U.S. The U.S. Centers for Medicare & Medicaid Services (CMS) allow (but do not compel—) physician groups of at least 200 eligible professionals filing under the same tax identification number to report as groups rather than as individuals. The number of measures and the scope of quality assessment continue to be expanded each year. The measures and normative target levels for each measure are curated by various 'steward' organizations such as the National Quality Foundation (NQF), the Joint Commission on Accreditation of Health Organizations (JCAHO), the National Committee for Quality Assurance (NCQA), and others. While manual, paper-based reporting of providers' performance according to each applicable Clinical Quality Measure is still permitted, increasingly most providers are utilizing electronic methods for reporting, wherein their performance results are computed from data retrieved from online electronic health records (EHR) systems. Such computer-based online calculation and reporting methods are termed Electronic Clinical Quality Measures (eCQM).

The CQM, eCQM, P4P, and P4V measures, or MU measures and similar performance measures are an aspect of health care reform wherein a diverse array of clinical safety and effectiveness measures relating to clinical processes and outcomes are utilized to financially incentivize the delivery of health services in such a way as to achieve desirable clinical outcomes via efficacious processes, toward the improvement of individual benefits and societal value from the care services rendered. However, the methods and technologies utilized for determining conformity to these measures suffer from imprecision, unreliability, and inaccuracy. That is, while attempts have been made to provide a technological solution to improve decision support systems to overcome these deficiencies, conventional technology has largely failed to provide a reliable and accurate solution. As such, new and improved techniques, such as described herein, are needed to address the deficiencies of the prior technologies.

SUMMARY

A technology is provided for applying Electronic Clinical Quality Measures (eCQM), Pay-for-Performance (P4P) measures, Meaningful Use (MU), or similar measures in human health care in a fantasy league exchange. For example in one embodiment, an apparatus utilizes statistical regression or related methods to establish performance rankings of provider individuals or groups during a measurement time period. Further, in some embodiments, the apparatus utilizes Bradley-Terry regression that is optionally parallelized so as to determine statistical associations with such factors as clinician, care venue, and patient attributes successfully and quickly, despite the fact that the number of competitors evaluated may be large. Statistical associations and coefficient values from the regressions may be used to forecast or project a future time period's performance results for selected individual or group competitors and/or to provide comparative rankings for purposes of informing decisions regarding draft picks, roster submission, or bets placed in a fantasy league exchange system for health services. In this way, embodiments of the disclosure may serve to intensify the efforts toward improving the clinical safety and outcomes quality of health service delivery, improving the provisioning of fair and equitable access to health services particularly for underserved populations, and improving the cost profile and cost-effectiveness of such services.

Accordingly, in an embodiment as will be further described herein, operation of a fantasy league exchange for health services is enabled from determining statistical association relationships among explanatory variables that predict future comparative performance and rankings of clinician EPs based on published eCQM performance measures. A provider clinician population, patient population, and the eCQM performance measures to be used in ranking analysis are selected. The patient population may be determined by inclusion-exclusion criteria. eCQM performance data is identified and accessed for applicable prior measurement interval(s) meeting the selection criteria, and may include positive/negative (e.g., "winner"/"loser") outcomes for applicable patient-provider pairs. Explanatory attributes to be included as independent variables in models also may be selected. In some embodiments, one or more "missingness rates" for the selected explanatory variables and binary outcome variable(s) may be determined; for instance in an embodiment, cases for which the outcome variable is missing may be excluded, and/or missing values or exclude cases for which more than 10% of explanatory variables' values are missing may be imputed.

Next, Bradley-Terry regression, logistic regression models, or other classification models, such Support Vector Machine, or Neural Network, for instance, are determined from the selected criteria and corresponding data, and model convergence is determined. The statistical significance of model coefficients are then determined. In an embodiment, AIC values are used to determine the statistical significance for the one or more alternative models. Based on the determined statistical significance, the best-performing model is selected and stored for the selection criteria, explanatory variables, and per-period positive/negative (e.g., "winner"/"loser") outcomes for selected provider pairs. Finally, provider rankings are provided to a fantasy exchange system, which may be used by authorized subscriber(s)/user(s) in preparing line-up rosters and decisions regarding entry and wagering transactions. In some embodiments, a corresponding explanatory analysis for the statistically significant associations is also provided.

BRIEF DESCRIPTION OF THE DRAWINGS

The present invention is described in detail below with reference to the attached drawing figures, wherein:

FIGS. 4A-4D illustratively provide an example embodiment of a computer program routine for performing parallelized Bradley-Terry modeling of eCQM performance for fantasy health wagering; and FIGS. 5A-5B illustratively depict an example embodiment of a computer program routine for determining correlation between the providers' Physician Quality Reporting System (PQRS) participation and Meaningful Use electronic health record (EHR) certification, in accordance with an embodiment of this disclosure.

DETAILED DESCRIPTION

Figure 1A:
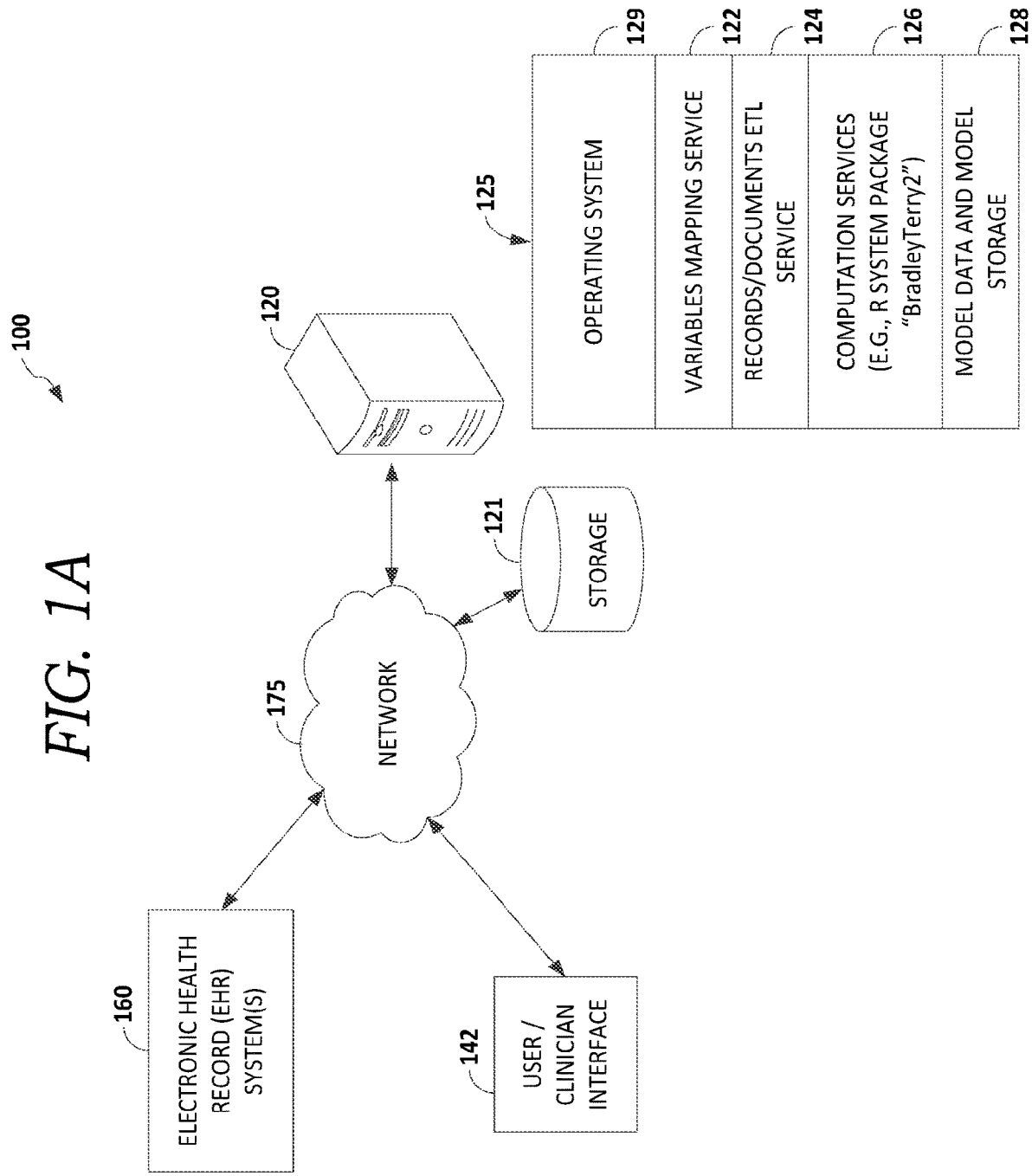
FIGS. 1A and 1B depict aspects of an illustrative architecture suitable for practicing an embodiment of the invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media. As such, computer readable media may be specifically purposed or specially programmed to employ the specific techniques and logical structures described herein. Upon being specifically programmed with the logical structures described in the present application, embodiments may provide for enhanced decision support systems that are capable of the precision, reliability, and accuracy that was previously unattainable by conventional computers.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other computer hardware or storage devices. These technologies can store data momentarily, temporarily, or permanently.

As described above, CQM, eCQM, P4P, and P4V and similar performance measures are an aspect of health care reform wherein a diverse array of clinical safety and effectiveness measures relating to clinical processes and outcomes are utilized to financially incentivize the delivery of health services in such a way as to achieve desirable clinical outcomes via efficacious processes, toward the improvement of individual benefits and societal value from the care services rendered.

'Meaningful Use' (MU) measures are one component of this aspect of health reform. 'Meaningful Use' measures generally refer to performance metrics that are used in ascertaining clinical outcomes, effectiveness, or process quality associated with clinicians' utilization of electronic health record (EHR) systems that are intended to support evidence-based best care practices, lower variability or inconsistency in care content, and the ability to measure attributes of the care delivered so as to establish accountability for that care, which in turn can be a basis for payment incentives and penalties for superior and inferior care quality, respectively. In other words, 'Meaningful Use' measures refer to the context of using EHR software systems to conduct and document the process of care delivery. The establishment of eCQM and P4P and MU measures for mental health and addiction medicine was a late addition to health care reform regulations in the U.S.

In general, eCQM and P4P and MU are salutary policies with a variety of quality and safety benefits for the public health. However, the fact that some disciplines, such as alcoholism and drug addiction treatment are often "one-time" treatments and tend to experience relatively modest numbers of newly-incident patients per year and the clinicians who treat these patients may not have multi-year longitudinal engagement with these patients means that the accuracy and statistical reliability of the measures may not be as stable and fair as is the case for other chronic medical ambulatory care sensitive conditions ("ACSCs") such as asthma or hypertension or hyperlipidemia or heart failure or diabetes, all of whose management involves numerous episodes of care provisioned over periods of multiple years and whose management is never "one-time" treatment.

Further, it is common that a certain amount of item-nonresponse or missingness is present in the published eCQM data. The circumstances where this arises are several—including recent entry of a clinician into a field of practice or a new venue of practice, such that accruals of patient cases on which to determine eCQM performance are not yet sufficient for comparison purposes; temporary suspension of practice activities by an individual clinician during a measurement period or a significant portion of a measurement period, for administrative or other reasons, followed by resumption of the practice activities that are the subject of performance evaluation and ranking; or excursions between a clinician's decision to file as an individual EP versus filing as a member of a group practice EP.

A significant problem of conventional approaches related to ranking competitors for formulating rosters of players in fantasy sports exchanges are (a) that they are not robust against contingent missingness of certain player performance measures and (b) that they are able only to reliably and quickly compute rankings for relatively small-cardinality universes comprising at most a few hundreds of competitors and are unable to accommodate large-cardinality universes of tens or hundreds of thousands of competitors.

Embodiments of the present disclosure address this problem and improve the field of clinical therapeutics and safety and effectiveness measurement, through the fantasy league exchange. Further, embodiments enable a fast and reliable Bradley-Terry type statistical regression on large-cardinality cohorts of clinician competitors and their eCQM performance measures, in a manner that is robust against a moderate amount of item-nonresponse or contingent missingness in the input data.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running aspects of this disclosure, which in some embodiments may include collecting and analyzing unstructured text data from electronic health record(s), which may include claims data, to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Operating environment 100 is one example of a suitable environment and system architecture for implementing an embodiment of the disclosure. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems; and may be implemented in computer system 120. Similarly, EHR system 160 may perform functions for two or more of the EHR systems (not shown). In an embodiment, EHR system 160 includes historical claims data for health services, apportionment data, and related health services financial data.

In some embodiments of the disclosure, sequence itemset mining is performed using data about a population of patients derived from patient EHR information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as wearable, bedside, or in-home patient monitors or sensors, for example.

Example operating environment 100 further includes provider user/clinician interface 142 communicatively coupled through network 175 to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient, set of patients, or provider clinicians, according to the embodiments presented herein. Embodiments of interface 142 also facilitates accessing and receiving information from a user or health care provider about a specific patient or population of patients including patient history; health care resource data; variables measurements, timeseries, and predictions (including plotting or displaying the determined outcome and/or issuing an alert) described herein; or other health-related information, and facilitates the display of results, recommendations, or orders, for example. In an embodiment, interface 142 also facilitates receiving orders for the patient from the clinician/user, based on the results of monitoring and predictions. Interface 142 may also be used for providing diagnostic services or evaluation of the performance of various embodiments.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on interface 142. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interface 142. In some embodiments, interface 142 operates in conjunction with software stack 125.

In embodiments, variables mapping service 122 and records/documents ETL service 124 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages including, in an embodiment, package BradleyTerry2 used for Bradley-Terry modeling, including structured versions in which the parameters are related to explanatory variables through a linear predictor and versions with contest-specific effects, natural language processing services (not shown) such as Discern nCode™ developed by Cerner Corporation, or similar services. In another embodiment, computation services 126 may utilize the R package 'speedglm' and glm on Hewlett Packard Distributed R, Revolution Analytics, GLMRegressionModel.scala on Apache spark, or other parallelized glm implementations. In an embodiment, computation services 126 include the services or routines, which may be embodied as one or more software agents or routines such as the example embodiments of computer program routines illustratively provided in FIGS. 4A-4D and 5A-5B. In some embodiments, computation services 126 use EHR 160 and/ or model data and model storage services 121. Some embodiments of stack 125 may further use Apache Hadoop and Hbase framework (not shown), or similar frameworks operable for providing a distributed file system, and which in some embodiments facilitate provide access to cloud-based services such as those provided by Cerner HealtheIntent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium® Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
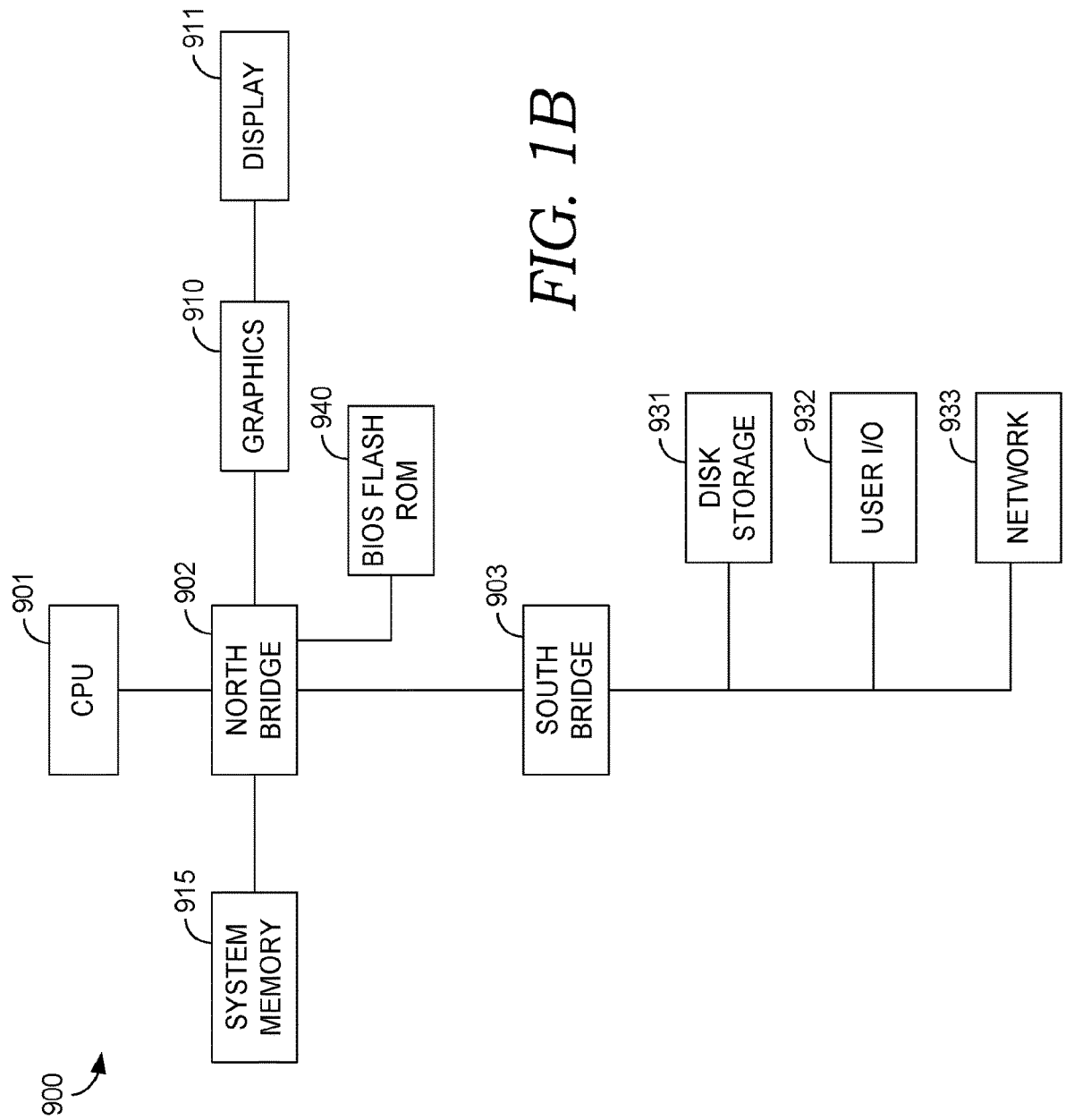

Turning briefly now to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
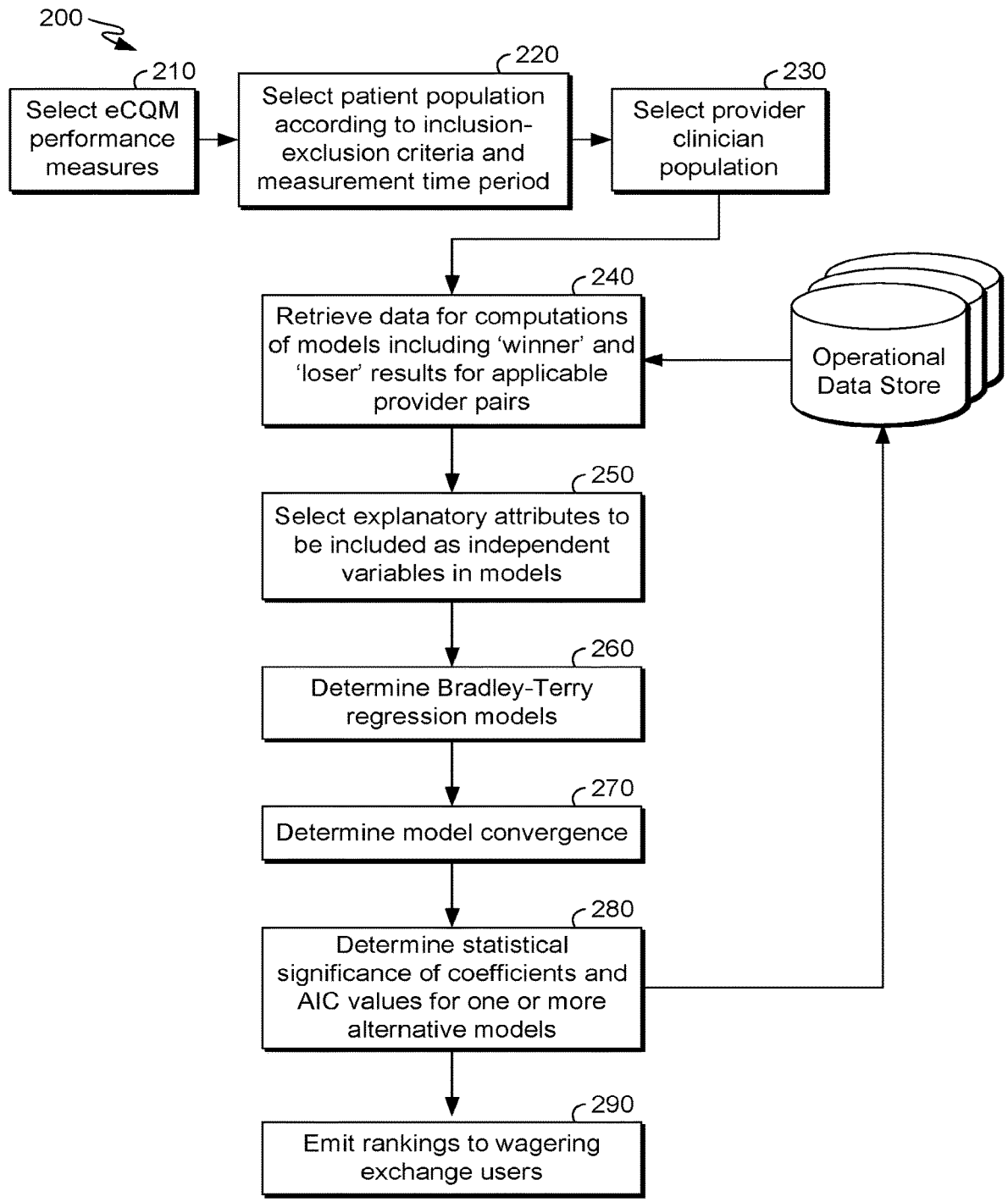
FIG. 2 depicts a flow diagram of an exemplary method for performing statistical regression by Bradley-Terry regression and beta regression methods for paired comparisons.
Figure 3:
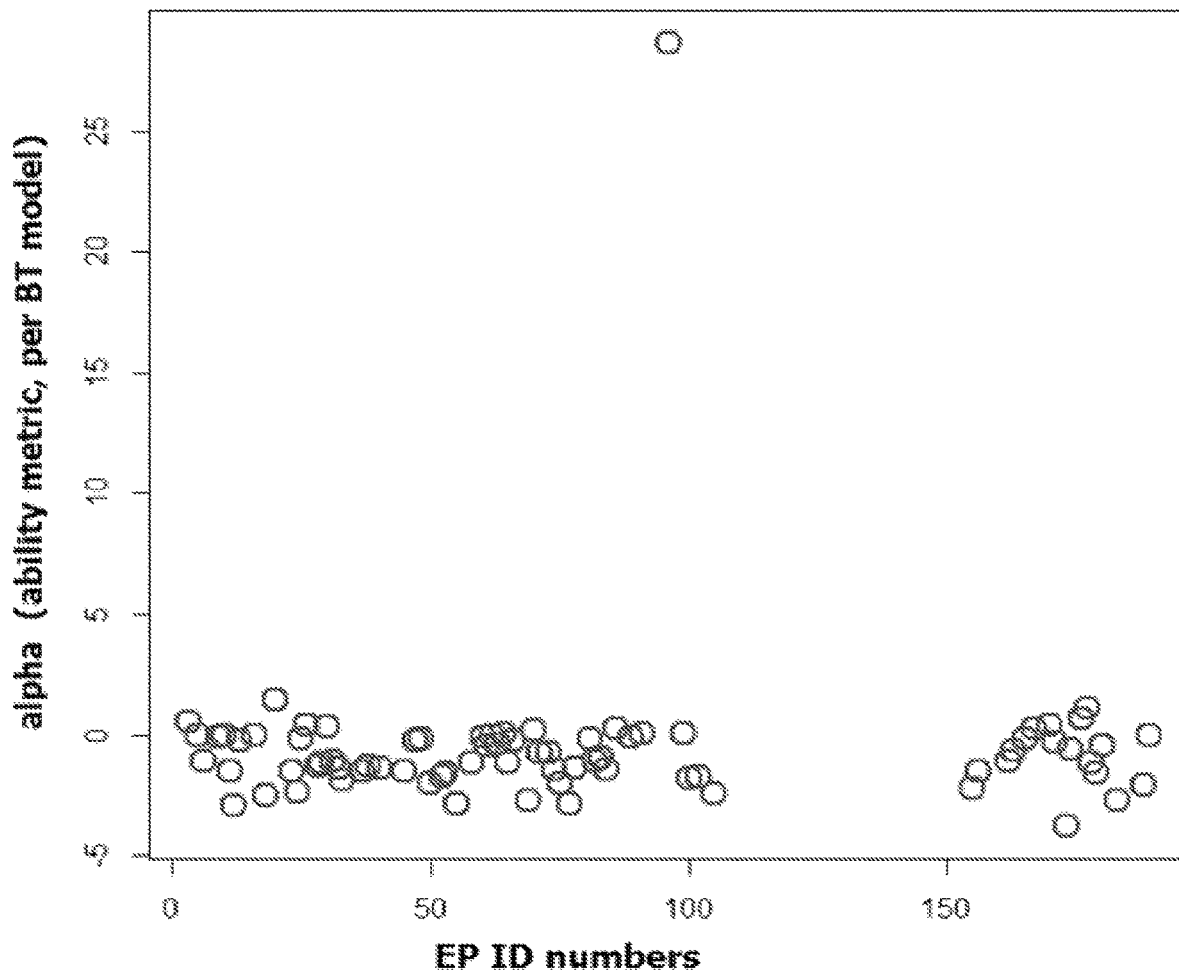
FIG. 3 depicts an example of endocrinologist performance for an embodiment of this technology reduced to practice.

With reference now to FIGS. 2, 3, 4A-4D, and 5A-B, a flow diagram is provided in FIG. 2 illustrating a method 200 of modeling eCQM pair comparisons by performing statistical regression by Bradley-Terry regression and beta regression methods for paired comparisons for determining rankings for use by to wagering exchange users in a fantasy health exchange. To date, no such fantasy league exchanges have been developed for parties interested in the comparative performance of eligible providers (EPs) of human health services. Various stakeholders who produce, consume, or finance health services may elect to participate in these fantasy league exchanges, using skill and insight regarding provider performance and patient populations to formulate virtual rosters of clinician providers (individual providers or, alternatively, group practices) and to submit said rosters to fantasy league exchanges and place wagers on the outcomes of clinicians' performance comparisons in future measurement periods. The systems and methods described herein enable the development and operation of such fantasy league exchange for health services by determining statistical association relationships among explanatory variables that predict future comparative performance and rankings of clinician EPs based on published eCQM performance measures.

For a sports fan, professional sports once meant merely an opportunity to attend games, to be an ardent fan of selected teams and players, and to second-guess the owners and managers of the teams. Then, in the 1920s, the company Ethan Allen released a table game called All-Star Baseball, which allowed baseball fans to simulate team management by choosing an hypothetical team from a collection of player cards and selecting the team's lineup. Each player's performance in All-Star Baseball was determined by probabilities that were derived from the players' actual past performances, in conjunction with the random event of rotating a spinner over these cards.

For decades, All-Star Baseball was the only way for sports fans to simulate team management. In 1961, Hal Richman introduced the simulation game, Strat-O-Matic Baseball, which included one playing card for each Major League Baseball player. Each card contained various ratings and result tables that corresponded to dice rolls. For each game, Strat-O-Matic participants selected teams and batting orders, rolled the dice, and then reviewed charts to determine game results. By the 1980s, many other companies had joined Strat-O-Matic in the simulation sports market, with some companies, such as Micro League Baseball and Avalon Hill, providing games digitally via a computer. One of the benefits of playing sports simulation games on the computer was the increased range of managerial options. In April 1980, a group of professional baseball enthusiasts assembled at the La Rotisserie Française restaurant in New York City to conduct the first Rotisserie League baseball player auction. To enter the auction, each of the league's ten participants posted $260. Each participant then used his $260 entry fee to compose a draft roster, bidding on players from Major League Baseball's National League rosters.

According to the original Rotisserie League rules, each participant earned points based on his selected players' real-life performances in eight statistical categories: four categories were based on hitting performance, and four were based on pitching performance. At the end of the Major League Baseball season, the Rotisserie League participant whose team earned the most points would receive a cash prize. With the Internet's facilitation of fantasy sports, by the mid-1990s a number of traditional sports and entertainment companies had begun to enter the online fantasy sports marketplace. The first of these companies to provide fantasy sports games on the web was the Entertainment Sports Programming Network ("ESPN"), which in 1995 launched its first entirely Internet-based fantasy baseball game. By the year 2000, ESPN had expanded its fantasy sports offerings into football, basketball, hockey, NASCAR, soccer, golf, and even fly fishing.

Today's fantasy participants play games in a wide range of different sports. Fantasy football is currently the most popular, with more than 35 million North American participants per year. Fantasy baseball is second in terms of popularity, with approximately 18 million annual participants. While most sports fans consider fantasy baseball to be the original fantasy sport, one of the challenges in building its popularity is the extended length of the Major League Baseball season, and the need for fantasy baseball owners to monitor their teams on a more frequent basis than owners in other fantasy games. Immediately behind fantasy baseball in popularity lie fantasy racing, basketball, and hockey. It is projected that daily fantasy games will generate approximately $3 billion in fees this year and grow 41% annually, reaching $14.4 billion in 2020.

In a fantasy sport, players may be allocated in four ways. A first way is through an auction. Traditional auctions, the type used by the Rotisserie League, involve a bidding process among participants for players, one player at a time. Each player is ultimately assigned to the participant that bids the greatest amount from a fixed sum of money for that player. This continues until every team has "purchased" a full roster of players. A second way that players may be allocated is through a "modified auction." In a modified auction, the price of each player is determined before the competition begins, and multiple participants in a single league may select the same player. The modified auction is especially useful in a short-duration league because it does not require all of the league's participants to simultaneously select players. However, the downside to a modified auction is that it removes the element of "trading" from fantasy sports because trading players would not make sense if a particular player is already on more than one team's roster.

A third way that players may be allocated is through a league draft. Draft leagues take their inspiration from the way in which new players are allocated in the majority of real, professional sports leagues. A fantasy sports league might begin a season with a draft, such as a "snake format draft," meaning that participants can select players in rotation, often with the same owner who selected first in round one, selecting last in round two, and vice-versa. The initial draft order, may be determined by a random event. However, in some instances, owners have the opportunity to express their preference for a particular draft position before the draft begins.

Finally, certain situations, fantasy participants can agree to have players allocated to their teams randomly by software, which may be provided by a host website associated with the league. For example, a growing number of host sites (such as ESPN.com), provide an "Autopick Draft Option," in which a computer program, rather than a participant, "automatically drafts players to each team in the league on a scheduled draft date." Despite the efficiency of the "Autopick Draft Option," this option remains relatively unpopular because it removes all skill from the drafting of players. Within each of these types of fantasy sports games, there are six different stakeholder groups involved in the action.

Additional aspects of suitable fantasy health exchanges utilizing provider rankings determined by the method 200 include:

1. Participants. Participants are the individuals who compete in the fantasy sports leagues. In 2015, there are almost 60 million people playing fantasy sports in the U.S. and Canada. 2. Host Sites. Some embodiments of a fantasy league may utilize a "host site." Host sites may comprise websites that store league data and serve as the place where participants make changes to their rosters. These sites may provide a platform for real-time statistical updates and tracking. In addition, a host site may collect league entry fees, distribute prize money, manage message boards, and provide expert analysis.

3. Commissioners. In some embodiments, each fantasy sports league has a commissioner. "Commissioners" are individuals who manage fantasy sports leagues by establishing league rules and resolving disputes over rule interpretations. 4. Treasurers. In some embodiments, such as fantasy sports leagues with entry fees and prize money, a treasure may be associated with the league for collecting money at the beginning of the season, and to distribute it to the winners at the season's end.

5. Strategic Advisors. Strategic advisors may not be officially associated with a league, but may make their living by providing advice to other fantasy sports participants. Much like stock analysts on Wall Street, such fantasy sports advisors devote their careers to following the performances of professional athletes in far greater detail than the average working professional could do independently. 6. Insurers. In some instances, an insurance market may be utilized to protect high-stakes fantasy sports participants from monetary loss in the event of an injury to a player on one's fantasy sports team.

In addition to financial opportunities that such fantasy league exchanges provide to (a) those who participate by posting entry and subscription fees and who formulate superior rosters and place successful wagers via the exchanges and (b) those who operate the exchanges or invest in exchange enterprises or advise or insure the exchanges or the participants, the operations may produce beneficial effects for the franchises and players whose performance is the object of the wagering activities. Benefits may arise in various ways, particularly in terms of favorable and intensified market visibility and preferences and spending patterns that are induced by media attention to the winning entities and to those whose fantasy league rosters included those entities. In a broader social sense, fantasy league-related market activity exerts new and intensified pressure for under-performers to improve their performance.

In the context of fantasy health exchanges, such pressure may accelerate changes in safety and quality and equitable access and health services efficiency that otherwise would be accorded less priority and less resources. In addition to these traditional methods of promotion, fantasy sports exchange enterprises have partnered with individual sports team franchises in major U.S. professional sports leagues. For example, DraftKings recently announced sponsorship agreements with 12 new NFL franchises, and earlier this year partnered with sports networks ESPN and FOX Sports.

In some instances, fantasy health exchange enterprises might partner with health provider enterprises and/or health insurance enterprises or health plans, with a comparable aim of driving new bookings, better and more loyal consumer member retention, improved health behavior compliance of the patient-fans who are wagering on rosters they have formulated that include provider clinicians who are delivering exemplary quality care to themselves or their family members, friends, and relatives, and the like. Further, fantasy health exchanges may induce beneficial effects in the underlying health services industry not only by rostering high-performing, "high-owned" players (i.e., providers), but also by "contrarian" rostering of "low-owned" players or players whose performance stats are trending up or down over a relevant span of time.

Turning now to FIG. 2 and method 200 for performing statistical regression by Bradley-Terry regression and beta regression methods for paired comparisons for determining rankings for use by to wagering exchange users in a fantasy health exchange. With reference to method 200, generally, a paired-comparison may be performed and may include supporting the contingent presence of "ties." In particular, in each of the selected paired comparisons (denoted by $(j_i|k)$) there are two possible outcomes in the ordinary case: agent j wins, jk(j), or agent k wins, jk(k). In other situations, provision is made for the possible occurrences of "ties" wherein agents j and k have identical performance, in which case there are three possible outcomes. For the analysis of such paired comparison data, a Bradley-Terry (BT) regression method may be utilized. However, in some embodiments, multivariable logistic regression, support vector machine (SVM), artificial neural network (ANN), Bayesian network, and other modeling methods may be used to establish statistical associations of explanatory variables with the binary (e.g. positive/negative) outcome variable.

Censoring of unlabeled cases (which may be embodied as rows in a table) for which the value of the outcome variable is missing, in general, may be necessary for the model generation step to succeed. Likewise, censoring of cases (rows) in which an excessive proportion of explanatory variables' values are missing is also necessary for the model generation step to produce reliable, accurate results. Alternatively, statistical multiple imputation methods may be utilized to produce plausible, unbiased estimates or substitute values for those explanatory variables whose values are missing.

At step 210, eCQM performance measures can be selected. Patient population can also be selected according to inclusion-exclusion criteria and measurement time period (step 220). Provider clinician population (step 230) who provided the services to the patients of step 220 can also be selected. Some embodiments of step 220 further include measuring the patient data for the patients meeting the inclusion-exclusion criteria for the measurement time period for each of the facilities and treating clinicians. At step 240, retrieve data for computations of models including binary results (e.g., a positive or a negative result) for applicable provider pairs corresponding to the selections of steps 220 and 230. Embodiments of step 240 retrieve eCQM performance data for applicable prior measurement interval(s) meeting selection criteria.

At step 250, select explanatory attributes to be included as independent variables in the models. Some embodiments of step 250 may include determining or selecting attribute variables to be included in statistical models of eCQM, MU, or P4P performance, and assembling attribute variables' values for the patients and provider clinicians. Some embodiments of step 250 comprise determining missingness rates for selected explanatory variables and positive/negative outcome variable(s), exclude cases for which the outcome variable is missing, and/or impute missing values or exclude cases (rows) for which more than 10% of explanatory variables' values are missing.

At step 260, Bradley-Terry regression models (or other classification models, such as logistic regression models, Support Vector Machine, Neural Network, or the like) are determined. Some embodiments of step 260 may be performed using the Bradley-Terry2 R-package of software services 126 (described in connection to FIG. 1A) as illustratively shown in FIGS. 4A-4D. In particular, aspects of method 200, including step 260, may be carried out using the computer program provided in FIGS. 4A-4D. At step 270, model convergence is determined, and at step 280, statistical significance of model coefficients via AIC values for one or more alternative models are determined. In some embodiments of step 280, the best-performing model is determined, which may be determined based on the statistical significance, and the model may be stored for selection criteria and explanatory variables and per-period positive/negative outcomes for selected provider pairs.

At step 290, provider rankings are provided to the fantasy exchange system for use by subscriber(s)/user(s) in preparing line-up rosters and decisions regarding entry and wagering transactions. Some embodiments of step 290 further include preparing corresponding explanatory analysis for the statistically significant associations, and providing these.

EXAMPLE REDUCTION TO PRACTICE

Aspects of an embodiment reduced to practice using method 200 are illustratively provided in FIGS. 3, 4A-4D, and 5A-5B, which include respectively: a graph from an example embodiment reduced to practice and applied to endocrinologist performance in diabetes showing ability metric per Bradley-Terry model versus endocrinologist performance (EP) ID numbers based on the computer program routine of FIGS. 4A-4D; a computer program routine for performing parallelized Bradley-Terry modeling of eCQM performance for fantasy health wagering; and a computer program routine for determining correlation between the providers' Physician Quality Reporting System (PQRS) participation and Meaningful Use electronic health record (EHR) certification. It should be appreciated that conventional methods and systems have generally been incapable of determining this same result. As such, by supplying unique determinations, the current embodiments are capable of providing significant technological advantages over conventional technology.

With continuing reference to the drawings, the example embodiment reduced to practice is now described. Reduction to practice was accomplished using a computer running the Linux operating system, the open-source statistical software package R, and the R module 'BradleyTerry2. However, a cloud-based computing configuration is one alternative preferred embodiment. Other embodiments were achieved using the R package 'speedglm' and glm on Hewlett Packard Distributed R. Similar embodiments might be arranged using Revolution Analytics, GLMRegressionModel.scala on Apache spark, or other parallelized glm implementations.

For the reduction to practice, an observational study of was performed using the 2014 and 2015 National public data sets provided by the CMS Medicare Physician Compare system (available at https://data.medicare.gov/data/physician-compare). In the 2014 data, there were 890,707 distinct clinicians whose registrations and data were contained in the Physician Compare public database, and in 2014 there were 905,136. Despite the term 'physician' in the name of the CMS system, the database actually contains information on individuals practicing a wide variety of clinical specialties. U.S. clinicians are required to register in the system in order to receive CMS payments related to PQRS. Registration involves identification by National Provider ID (NPI), PAC ID, and a unique Professional Enrollment ID.

Specialties in the Physician Compare public database presently include the following 77: Addiction Medicine, Allergy/Immunology, Anesthesiology, Anesthesiology Assistant, Audiologist, Cardiac Electrophysiology, Cardiac Surgery, Cardiovascular Disease (Cardiology), Certified Nurse Midwife, Certified Registered Nurse Anesthetist, Chiropractic, Clinical Nurse Specialist, Clinical Psychologist, Clinical Social Worker, Colorectal Surgery (Proctology), Critical Care Medicine (Intensivists), Dermatology, Diagnostic Radiology, Emergency Medicine, Endocrinology, Family Practice, Gastroenterology, General Practice, General Surgery, Geriatric Medicine, Geriatric Psychiatry, Gynecological Oncology, Hand Surgery, Hematology, Hematology/Oncology, Hospice/Palliative Care, Infectious Disease, Internal Medicine, Interventional Cardiology, Interventional Pain Management, Interventional Radiology, Maxillofacial Surgery, Medical Oncology, Nephrology, Neurology, Neuropsychiatry, Neurosurgery, Nuclear Medicine, Nurse Practitioner, Obstetrics/Gynecology, Occupational Therapy, Ophthalmology, Optometry, Oral Surgery (Dentist), Orthopedic Surgery, Osteopathic Manipulative Medicine, Otolaryngology, Pain Management, Pathology/Laboratory Medicine, Pediatric Medicine, Peripheral Vascular Disease, Physical Medicine and Rehabilitation, Physical Therapy, Physician Assistant, Plastic and Reconstructive Surgery, Podiatry, Preventative Medicine, Psychiatry, Pulmonary Disease, Radiation Oncology, Registered Dietitian or Nutrition Professional, Rheumatology, Single or Multispecialty Clinic or Group Practice, Sleep Laboratory Medicine, Speech Language Pathologist, Sports Medicine, Surgical Oncology, Thoracic Surgery, Undefined Non-Physician Type, Undefined Physician Type, Urology, and Vascular Surgery.

The CMS Physician Compare database is currently updated on a quarterly basis (four times each year). As the scope of the U.S. pay-for-performance health finance regime is widened and the number of eCQM measures increases, it is likely that the frequency of updates may increase beyond quarterly. However, weekly or daily updates may be inappropriate or impractical. A quarterly frequency may be sufficient to support a vibrant exchange, not unlike trading in certain securities options or commodity futures which have quarterly contract dates.

In this actual reduction to practice of an embodiment of this disclosure, the Pearson correlation between the providers' PQRS participation and Meaningful Use EHR certification was 0.18 in 2014 and 0.31 in 2015, respectively. In a selected population of endocrinologists for whom 2015 eCQM diabetes outcome performance measures and Medicare 5-Star performance measures were available, Bradley-Terry regression was performed. Three eCQM out of 14 measures were found to be statistically significant at the $p<0.05$ level and strongly predictive of individual and group Pay-for-Performance positive status in the results published by CMS for the third quarter measurement period of 2015. As illustrated in this reduction to practice, whereas conventional technology might have failed at accurately providing a positive pay-for-performance status, current embodiments are capable of identifying particular eCQM measures that were strongly predictive of individual and/or group Pay-for-Performance status. This is one of the many ways that embodiments described herein are an improvement over conventional technology. It should be appreciated that the deficiencies of conventional technology cannot be overcome by simply using a computer and/or any other technological environment. This is because conventional methods, even if employed by a computer, are generally incapable of achieving the accuracy of the current embodiments.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

Embodiment 1. A method for evaluating a medical therapy with a computing device, the method comprising: accessing, with the computing device, a data storage system to obtain baseline characteristics for members of a population of patients who each receive a therapy or a bundle comprised of a plurality of therapies; accessing, with the computing device, the data storage system to obtain baseline characteristics and information regarding members of a population of clinician providers who deliver said therapies; accessing, with the computing device, the data storage system to obtain outcome characteristics and information regarding patients treated with the therapies by a set of clinician providers; accessing a data storage system containing published performance statistics regarding a plurality of Clinical Quality Measures to obtain an indication of a statistical association between at least one of the therapies and at least one aspect of the baseline characteristics and at least one of the outcomes in the subset of the population; accessing a data storage system containing published performance statistics regarding a plurality of performance measures for selected pairs of individual and group providers from which pairwise superior and inferior status ("winners" and "losers") may be ascertained; statistically modeling, with the computing device, the association between the quality measures and the superior or inferior status of the providers so as to produce rankings or forecasted projections of future rankings of the providers; connecting via internet or other computer network to one or a plurality of fantasy league exchanges; emitting rankings to users of fantasy league exchange apparatus, for purposes of informing their selection of rosters of individuals or groups to tender in fantasy league transactions.

Embodiment 2. The method of embodiment 1, further comprising analyzing the patient-provider-outcomes statistical associations by Bradley-Terry regression methods or beta regression methods or generalized linear modeling methods.

Embodiment 3. The method of embodiment 1, further comprising analyzing the patient-provider-outcomes statistical associations by Bayesian Markov Chain Monte Carlo (MCMC) Gibbs Sampler methods.

Embodiment 4. The method of embodiment 1, wherein the at least one outcome is associated with the therapy.

Embodiment 5. The method of embodiment 1, wherein modeling the distribution of the winning outcome for selected pairs of providers in the population includes evaluating alternate-payment or 5-Star or other performance measures.

Embodiment 6. The method of embodiment 1, wherein modeling the distribution includes methods for accommodating zero-inflation and, optionally, one-inflation.

Embodiment 7. The method of embodiment 1, wherein modeling the distribution via MCMC involves a "burn-in" series of iterations of sampling to stabilize the sampling process, preferably not less than 1,000 iterations, from which the resulting sampled values are discarded.

Embodiment 8. The method of embodiment 1, wherein modeling the distribution via MCMC involves a series of iterations subsequent to the iterations of embodiment 1, preferably not less than 4,000 iterations, from which the resulting sampled values are retained for calculating descriptive statistics.

Embodiment 9. The method of embodiment 1, further comprising calculation of the coefficients of the linear or nonlinear equations comprising the model relating the dependent outcome variable to the one or more independent explanatory variables, including provider characteristics, patient characteristics, facility characteristics, or other factors.

Embodiment 10. The method of embodiment 1, further comprising calculation of the parameters of a parametric distribution, such as the beta distribution for the distribution of statistical values of the outcome variable.

Embodiment 11. The method of embodiment 1, wherein the at least one aspect of the baseline characteristics includes one or more of a group consisting of: provider identity; provider specialty; a metric of the skill of the provider associated with the provisioning of the therapy services; provider annualized volume of therapy instances provided; provider venues of service delivery or clinic location.

Embodiment 12. The method of embodiment 1, wherein the at least one post therapy outcome includes one or more of a group consisting of: time to first occurrence of an event; a proportion of patients with a given outcome at a certain point in time; a proportion of patients with a defined plurality of outcome events; a proportion of patients with a defined frequency of outcome events; a patent questionnaire; a clinician patient evaluation; and a medical test result.

Embodiment 13. The method of embodiment 1, wherein values for one or more Clinical Quality Measure items for a given provider are missing or unmeasured in one or a plurality of measurement periods.

Embodiment 14. The method of embodiment 1, wherein the computations are parallelized among a plurality of processors such that the solutions of the statistical models may be determined more rapidly than would be possible on a single processing apparatus.

Embodiment 15. The method of embodiment 14, wherein the parallelization of the computations is performed by a cloud-based or other distributed collection comprising a plurality of processors whose joint operation is coordinated over a perhaps large physical distance via message-passing mediated by internet or other network connections.

Embodiment 16. The method of embodiment 14, wherein the parallelization of the computations is performed by a collection comprising a plurality of processors whose joint operation is coordinated via shared memory over modest physical distance.

Embodiment 17. The method of embodiment 1, wherein the performance measures of each distinct provider are measured and published in machine-readable format and made available via an online system and updated for each performance measurement period.

Embodiment 18. The method of embodiment 1, wherein the performance measures of a provider may be amended or updated for one or a plurality of performance measurement periods.

Embodiment 19. The method of embodiment 1, wherein a performance measure for a provider and a particular measurement period and population of patients and venue or geographic district has at any time a single published value, such that there are not multiple extant conflicting published measurements for said provider, period, population, venue or district.

Embodiment 20. The method of embodiment 1, wherein the modeling method uses ties for selected pairs of provider clinicians.

Embodiment 21. The method of embodiment 20, wherein the ties are handled using the Rao or Dittrich methods.

It will be understood that certain features and subcombinations are of utility and may be employed without reference

What is claimed is:

1. One or more non-transitory computer-readable media having computer-executable instructions embodied thereon that when executed by at least one processor, facilitate a method for determining provider rankings in a fantasy health exchange, the method comprising:
   determining a set of patient data for patients meeting an inclusion-exclusion criteria, the set of patient data corresponding to a time interval of treatment of the patients by a population of clinicians;
   receiving performance data for the population of clinicians based on the set of patient data and the time interval;
   determining, by distributing and performing parallelized determinations among a plurality of processors at multiple locations, a provider ranking in the fantasy health exchange, wherein the parallelized determinations among the plurality of processors at the multiple locations comprises:
      determining explanatory attributes to be included as independent variables in a classification model;
      determining the classification model using the explanatory attributes and the performance data; and
      based on the classification model, determining the provider ranking; and
   utilizing the provider ranking in the fantasy health exchange.

2. The one or more non-transitory computer-readable media of claim 1, wherein determining the classification model further comprises:
   determining a plurality of classification models using the explanatory attributes and the performance data;
   for each of the plurality of classification models, determining a statistical significance of classification model coefficients;
   determining model convergence for each of the plurality of classification models; and
   based at least in part on the determined model convergence for each of the plurality of classification models, determining which of the plurality of classification models is a best-performing model and selecting the best-performing model as the classification model.

3. The one or more non-transitory computer-readable media of claim 2, further comprising determining the provider ranking based on the statistical significance of the classification model coefficients for the best-performing model.

4. The one or more non-transitory computer-readable media of claim 1, wherein the classification model is determined based on a first statistical significance of coefficients of the classification model compared to a second statistical significance of coefficients of another classification model.

5. The one or more non-transitory computer-readable media of claim 4, wherein the first statistical significance is determined using Akaike information criterion values.

6. The one or more non-transitory computer-readable media of claim 5, wherein the second statistical significance is determined using Bayesian Markov Chain Monte Carlo Gibbs Sampler methods.

7. The one or more non-transitory computer-readable media of claim 4, wherein the classification model determined based on the first statistical significance is further stored for selected healthcare provider pairs for at least one of the following: a future selection criteria, explanatory variables, per-period positive outcomes, and per-period negative outcomes; the selected healthcare provider pairs corresponding to the patients.

8. The one or more non-transitory computer-readable media of claim 7, wherein the classification model comprises at least one of the following: a Bradley-Terry regression model, a logistic regression model, a Support Vector Machine, and a Neural Network.

9. The one or more non-transitory computer-readable media of claim 1, wherein the performance data comprises a binary outcome associated with a particular treatment that includes a positive outcome and a negative outcome.

10. A method for determining provider rankings in a health exchange, the method comprising:
    receiving a set of patient data for patients, the set of patient data corresponding to a time interval of treatment of the patients by a population of clinicians;
    receiving performance data for the population of clinicians based on the set of patient data and the time interval;
    determining, by distributing and performing parallelized determinations among a plurality of processors at multiple locations, a provider ranking in the health exchange, wherein the parallelized determinations among the plurality of processors at the multiple locations comprises:
       determining explanatory attributes to be included as independent variables in a classification model;
       determining the classification model using the explanatory attributes and the performance data; and
       based on the classification model, determining the provider ranking; and
    utilizing the provider ranking in the health exchange.

11. The method of claim 10, wherein determining the explanatory attributes comprises assembling values of variables associated with the set of patient data and the performance data.

12. The method of claim 10, further comprising determining a missingness rate for sets of the explanatory attributes and excluding values of a set of the explanatory attributes that has the missingness rate above a threshold.

13. The method of claim 10, wherein receiving the set of patient data for the patients further comprises:
    obtaining outcome characteristics of the patients based on a particular treatment provided to the patients;
    determining an indication of a statistical association between the particular treatment and at least one of the outcome characteristics; and
    using the statistical association to determine the set of patient data.

14. The method of claim 10, wherein the plurality of processors at the multiple locations perform the parallelized determinations by joint operation that is coordinated via a shared memory.

15. The method of claim 10, wherein the classification model is determined based on a first statistical significance of coefficients of the classification model compared to a second statistical significance of coefficients of another classification model.

16. The method of claim 15, wherein the first statistical significance is determined by one or more of the following: Bradley-Terry regression methods, beta regression methods, generalized linear modeling methods, and Bayesian Markov Chain Monte Carlo Gibbs Sampler methods.

17. The method of claim 16, wherein the second statistical significance is determined by one or more of the following: the Bradley-Terry regression methods, the beta regression methods, the generalized linear modeling methods, and the Bayesian Markov Chain Monte Carlo Gibbs Sampler methods.

18. The method of claim 10, wherein receiving the set of patient data for the patients further comprises parsing a first data storage system to obtain baseline characteristics for the patients who each received a particular treatment, and wherein receiving the performance data further comprises accessing a second data storage system to obtain performance statistics for a plurality of Clinical Quality Measures (CQM).

19. The method of claim 18, further comprising obtaining the CQM for each provider of a plurality of providers having a number of positive outcomes associated with the particular treatment above a threshold.

20. A computerized system for determining provider rankings in a fantasy health exchange, the system comprising:
    at least one processor; and
    at least one computer storage media storing computer-useable instructions that, when executed by the at least one processor, cause the system to:
        determine a set of patient data for patients, the set of patient data corresponding to a time interval of treatment of the patients by a population of clinicians;
        retrieve performance data for the population of clinicians based on the set of patient data and the time interval;
        determine, by distributing and performing parallelized determinations among a plurality of processors at multiple locations, a provider ranking in the fantasy health exchange, wherein the parallelized determinations among the plurality of processors at the multiple locations comprises:
            determine explanatory attributes to be included as independent variables in a classification model;
            determine the classification model using the explanatory attributes and the performance data; and
            based on the classification model, determine the provider ranking; and
        utilize the provider ranking in the fantasy health exchange.

* * * * *